United States Patent [19]
Huck et al.

[11] Patent Number: 5,547,714
[45] Date of Patent: Aug. 20, 1996

[54] ION BEAM DEPOSITION OF DIAMOND-LIKE CARBON FILMS

[75] Inventors: Hugo A. Huck; Alberto E. Jech; Raúl Righini, all of Buenos Aires, Argentina

[73] Assignee: Comision Nacional de Energia Atomica, Buenos Aires, Argentina

[21] Appl. No.: 422,003

[22] Filed: Apr. 12, 1995

Related U.S. Application Data

[63] Continuation of Ser. No. 988,765, Dec. 10, 1992, abandoned.

[30] Foreign Application Priority Data

Dec. 23, 1991 [AR] Argentina ................. 321491

[51] Int. Cl.$^6$ ................... C23C 14/48; B05D 3/06
[52] U.S. Cl. ............ 427/523; 427/561; 427/577; 427/249; 427/255.5; 264/317; 423/446
[58] Field of Search ................. 427/523, 577, 427/255.5, 249, 122, 561; 204/192.16, 192.11; 264/317; 423/446

[56] References Cited

U.S. PATENT DOCUMENTS

| | | | |
|---|---|---|---|
| 4,822,466 | 4/1987 | Rabalais et al. | 204/192.15 |
| 4,935,303 | 6/1990 | Ikoma et al. | 428/408 |
| 5,055,318 | 10/1991 | Deutchman et al. | 427/38 |
| 5,185,067 | 2/1993 | Shibahara et al. | 427/523 |
| 5,192,523 | 3/1993 | Wu et al. | 427/523 |

FOREIGN PATENT DOCUMENTS 61-270370A  5/1985  Japan.
8802225  12/1988  WIPO.

OTHER PUBLICATIONS

"Chemical Effect of $CH_4^+$ Implantation into Iron, Nickel ans Alumium Thin Films", Chatterjee et al, Thin Solid Films, 167 (1988), 15, Mar., no. 2, pp. 211–218.

"Structure and Annealing Properties of Silicon Carbide Thin Layers formed by Implantation of Carbon Ions in Silicon", Kimura et al, Thin Solid Films 81(1981) pp. 319–327.

"Comparison of diamondlike coatins deposited with $C^+$ and Various Hydrocarbon ion beams", Antilla Koskinen et al. Applied Phys. Lett. 50 (3), 19 Jan. 1987, pp. 132–134.

A New Method for Making Long–Lived Carbon Foils ... I. Sugai et al, Nuclear Instruments & Methods Vol A–236 (1985) pp. 576–589.

Primary Examiner—Roy V. King
Attorney, Agent, or Firm—Kuhn and Muller

[57] ABSTRACT

A process forms an amorphous carbon film over a solid, which film has physical and chemical properties similar to those of diamond. Its ancillary objects are the solid bodies so coated and the self-sustained film obtained in a subsequent stage of dissolution of said substrate. The process includes generating a highly accelerated beam of carbon-hydrogenated ions, which beam is made to impact with sufficiently high energy on the surface of the substrate. The beam is concentrated by electrostatic lenses and homogenized by a magnetic mass separator. The process forms on a solid substrate, a film with properties similar to those of diamond, such as high hardness, high chemical stability, transparency, high heat conductivity and high electric resistivity; obtainable at ambient temperature, and which is simpler than known procedures.

7 Claims, 1 Drawing Sheet

ION BEAM DEPOSITION OF DIAMOND-LIKE CARBON FILMS

This application is a continuation of application Ser. No. 07/988,765, filed Dec. 10, 1992, now abandoned.

FIELD OF APPLICATION

The main goal of this present invention is to provide a procedure for forming an amorphous carbon film over a solid, which film has physical and chemical properties similar to those of diamond, such as hardness and durability.

Another object of this invention is the solid bodies so coated by applying this procedure.

Finally, another ancillary object is the self-sustained film obtained by applying this procedure on a solid substrate, continuing with a dissolution stage of the substrate.

Diamond is one of the crystalline forms of carbon, the least stable, whose properties are very well known. Outstanding among them are its hardness, its transparency, high refraction index, good thermal stability, high electrical resistivity, high thermal conductivity and the fact that it is chemically inert.

Another crystalline form of carbon, more stable, is that of graphite, but it's properties differ from those of diamond.

Numerous industrial activities require parts whose superficial characteristics are the same as those of diamond. Thus appeared the idea of covering parts made of other materials with films having these properties, e.g. for tool manufacture. Thus, not only are these coated materials more economic than natural diamond (which is expensive and difficult to process, especially when the parts are large), but the superficial properties can also be combined with the desired volumetric properties of the materials of the parts.

If, in addition, as is the case with this procedure, the films formed are smooth, without waviness, even smoothing out the small imperfections of the substrate. Therefore the applications of the present invention are quite wide.

Thus, the coated bodies can obtain properties of hardness and smoothness in order to be integrated in friction mechanisms such as, for example, shafts and/or bushing mechanisms with a high degree of precision, performance and/or reliability.

The same properties, combined with chemical inertness, can be used in the field of surgical prostheses. For example, the prosthetic knee-cap, which replaces the head of a femur, if made of a material which is sensitive to the biological substances present, may corrode and lose its smoothness, thereby starting to act as an abrasive within the cotyloid cavity of the iliac bone, which is partly cartilaginous. The same disadvantage happens if the prosthesis loses its smoothness because the material is soft; and all of the above is accelerated if the surface is wavy from the beginning. On the other hand, with the type of coating of the present invention, the abrasion of the cotyloid cavity does not take place.

Another application of the present invention, which can take advantage of the aforementioned properties along with transparency, is in the coating of lenses and other optical devices. A very fine coating, e.g. on the order of one micron, of amorphous carbon with a high degree of hardness, smoothness, chemical inertness and transparency, will protect costly lensed equipment against dust, sand, the action of acid traces, etc.

As will be seen below, it is possible to obtain a self-sustained amorphous carbon film, free from the solid on which it was formed, by diluting or melting the substrate. This film, duly sustained, has a few special applications, such as, for example, serving as stripper in certain types of particle accelerators, through which, when a highly accelerated atom passes, it completely loses its electrons.

STATE OF THE ART

In addition to covering surfaces with very small diamonds using glues, with results quite far from current requirements, it has already been attempted, by other procedures, to cover parts with a film with properties similar to those of diamond.

Among a multitude of more or less successful attempts, there are currently two procedures (with some variations which are industrially feasible.

One of these procedures is the so-called CVD (Chemical Vapor Deposition), which consists in generating a plasma of a hydrocarbon (generally methane), diluted in hydrogen, and depositing plasma ions over a substrate brought to a temperature on the order of 800° C., through an electric field. The limitations of this method arise, on one hand, from the need to heat the substrate, which limits the variety of materials that can be used and, on the other hand, the geometry of the part to be covered is also limited by the fact that the surface of the part must be an equipotential surface forming the electric field.

The second procedure consists in making deposits at ambient temperature, using carbon ion beams. To avoid graphitization of the deposit, it is simultaneously bombarded with an argon beam. The energy of both beams is on the order of 1 KeV.

The shortcoming of this method is that it requires two simultaneous ion beams, which makes it complicated and more expensive.

The procedure of the present invention overcomes the limitations and shortcomings of the known methods.

BRIEF DESCRIPTION OF THE INVENTION

The procedure for forming, on a solid substrate, a diamond-like carbon film with properties similar to those of diamond, is characterized as including the following stages:

a) cleaning and degreasing the outer surfaces of the solid substrate;

b) introducing the substrate in a first chamber, which is substantially at ground potential, with a layout which also includes an ion source at high positive voltage as compared to the ground, and a path between the ion source and the first chamber in which are found, at least, one set of electrostatic lenses and one magnetic mass separator;

c) creating a vacuum in the layout, on the order of $10^{-5}$ mbar;

d) generating a first ion beam of $C^+$, $CH_n^+$ ($n<5$) in the ion source, at a high positive voltage as compared to the ground;

e) forming and concentrating the first ion beam with the set of electrostatic lenses;

f) homogenizing the first beam with the magnetic mass separator, capable of deviating the undesired ions, obtaining a second ion beam with only $CH_3^+$ ions;

g) applying the second ion beam, by concentrating and homogenizing it in the mass separator, on the surface of the substrate, until it is covered with the film with properties similar to those of diamond. The ion source used in stage d) is preferably located in a second chamber, at high positive voltage as compared to the ground, in which there is a thermo-emitting hot filament, negative as compared to the walls of the second chamber, capable of providing electrons; the second chamber, equipped with a needle valve through which methane enters in a controlled manner; thus establishing an arc between the filament and the walls, which ionizes and fragments the methane molecules, producing $C^+$, $CH_3^+$ and $CH_4^+$ plasmas which, since they are positive, are strongly repelled and accelerated by the positive potential of the second chamber towards potentials closer to that of the grounds.

Since this is an innovative process as compared to the previous art, the main differences are explained below, with the clarification that there are other, unlisted, differences.

1) None of the known procedures includes homogenization of a ion beam by a magnetic mass separator.

2) None of the known procedures includes acceleration of a ion beam with electrostatic lenses, projecting it on a substrate in a chamber substantially at ground potential, thus allowing the substrate to be made of any material, electric conducting or insulating, not depending on the geometry of the substrate in order to generate the accelerating electric field. More homogeneous coating are thus obtained.

Furthermore, since ions have so much energy, some of them penetrate the substrate, forming an interpenetration or interface area, with an estimated thickness between 50 and 300 Å, which makes the carbon film adhere quite well to the substrate, its separation by mechanical means being impossible, except by destruction of the superficial layer (abrasion with diamond paste).

There are other methods, less preferable, for generating the first ion beams (e.g., made of another material, such as ethane, or with another energy source, such as radio frequency).

OBJECTS OF THE PRESENT INVENTION

Therefore, one object of the present invention is a procedure for forming, on a solid substrate, a film with properties similar to those of diamond; such as high hardness, high chemical and thermal stability, transparency, high heat conductivity and high electric resistivity.

Another object of the present invention is a procedure for forming, on a solid substrate, a film with properties similar to those of diamond, obtainable at ambient temperature, simpler than known procedures.

Another object of the present invention is a procedure for forming, on a solid substrate, a film with properties similar to those of diamond, which is smooth, and, furthermore, tends to smooth the small superficial imperfections of the solid substrates used.

Another object of the present invention is a procedure for forming, on a solid substrate, a homogeneous film with properties similar to those of diamond, regardless of the electric qualities of the substrate and its separator.

DETAILED DESCRIPTION OF THE DRAWINGS

Figure 1:
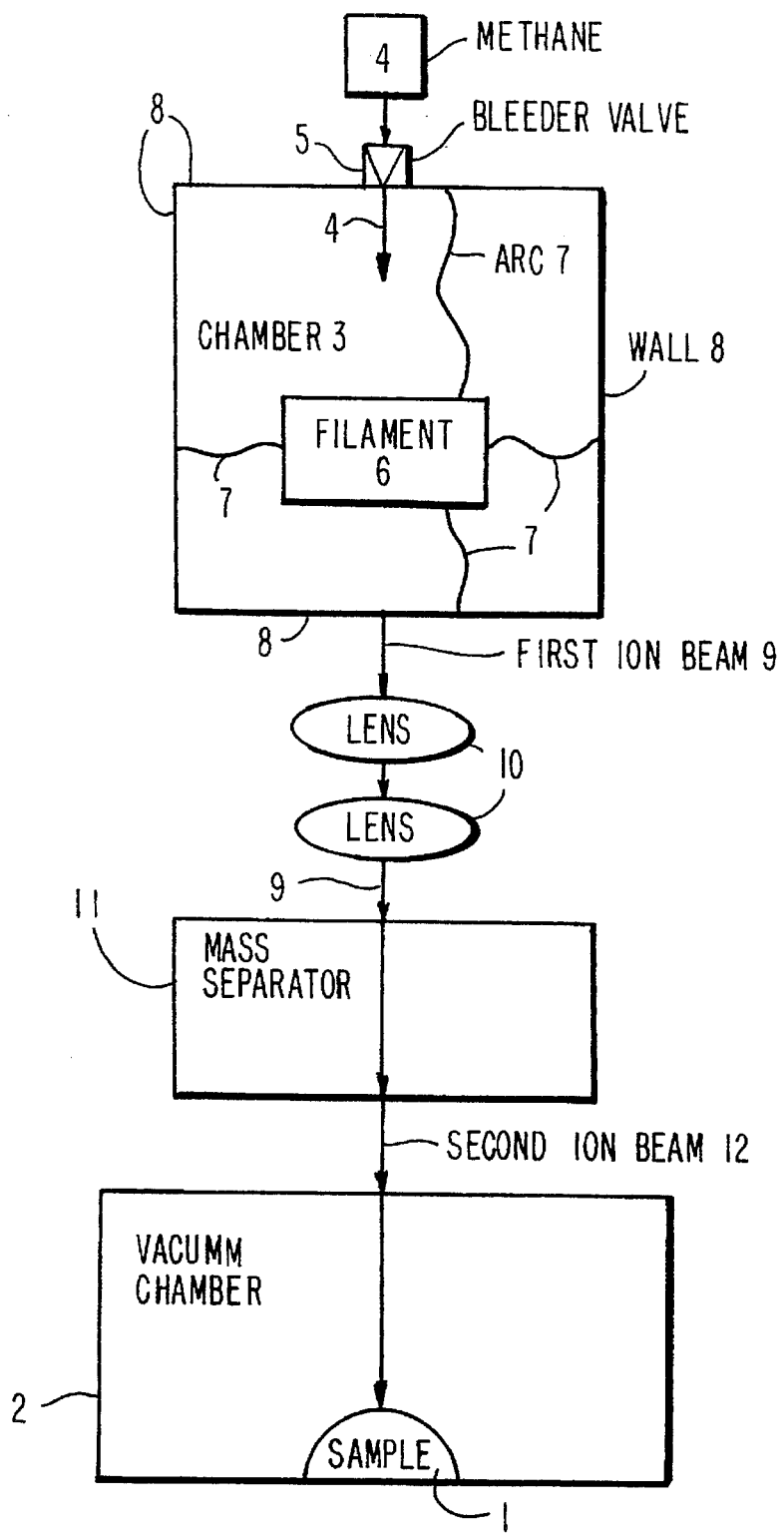
FIG. 1 is a schematic diagram of the process of the present invention.

As shown in FIG. 1, a solid substrate sample 1 is placed in a vacuum chamber 2 in which chamber 2a coating of solid substrate sample 1 is performed.

In another chamber 3, elevated to positive voltage as compared to the ground, methane 4 is introduced through a needle valve 5. With a hot filament 6, an arc 7 is created between the walls 8 of chamber 3, such that arc 7 ionizes and fragments the molecules of methane 4. An ion beam 9 is formed and is concentrated through electrostatic lenses 10, and introduced in a mass separator 11, allowing the formation of a high resolution second ion beam 12, which second beam only is applied to solid substrate sample 1.

EXAMPLE OF THE PRESENT INVENTION

To make clear the advantages summarily presented herein, to which users and specialists may add many more advantages, and in order to facilitate understanding of the features of the present invention, there is described below, as an example, an experiment conducted with the present invention. Precisely because this is an example, it should not be construed as limiting the scope of present invention, but the experiment is merely illustrative and explanatory of the basic concepts thereof.

To begin the experiment, a silicone crystal with (1,1,1) crystallographic orientation was polished to mirror quality and it was washed with degreasing substances under ultrasound exposure.

At the National Commission for Atomic Energy of the Republic of Argentina, the experiment was obtained from an isotope separator.

A solid substrate was placed in a vacuum chamber (on the order of $10^{-5}$ mbar) in which the coating was performed.

In another chamber, elevated to positive voltage as compared to the ground (variable between 1 and 70 keV), methane was introduced through a needle valve; with a hot filament, such as an electronic thermo-emitter, at lower voltage, an arc was created between the filament and the walls of the chamber, which ionized and fragmented the methane molecules, generating a C+, $CH_n^+$ plasma (n<5).

The ion beam was formed and concentrated through a system of electrostatic lenses, and was introduced in a double-focus Scandinavian-type mass separator, allowing high resolution separation of a specific ion, among others. Thus, the new $CH_3^+$ ion beam was homogenized, which, at energy level between 1 and 30 KeV, was applied onto one face of the sample at a current on the order of 2 μA for 10 hours.

After obtaining the coating, it was analyzed.

The material with the properties closest to those of diamond appeared to be that obtained at energies of 30 KeV; as noted by the data obtained for this case, which data is presented below.

By ellipsometric methods and an Elastic Recoil Detection Analysis (ERDA), a thickness of 0.3μ and a refraction index of 2.2 were measured, at a wave length of 5500 nm. With this data, resistivity was measured, and it appeared to be $10^{12}$ Ωcm.

Hardness was determined on the Mosh scale, by an attempt to scratch the film formed with materials of known hardness; and a value of 9 was obtained.

It must be noted that other hardness measurements, based on impact, do not apply, due to the reduced thickness of the film formed.

By Raman spectroscopy (using the 5145 Å line of an argon LASER, the dispersed light was analyzed in a 90 degree geometry, with a Jarrell-ASH 25-300 spectrometer).

It was determined that the film was amorphous, with a mix of SP2 and SP3 bonds.

These measurements were repeated after the sample was brought to a temperature of 700° C. in a nitrogen atmosphere, for 30 minutes. Graphite was found to appear.

The surface was subjected to the action of hydrochloric, sulfhydric, sulfuric and nitric acids, as well as sodium hydroxide, with negative reaction. It was observed that, as with diamond, the surface could be oxidized with potassium bichromate and sulfuric acid at 200° C.

By direct observation with the electronic microscope, it was seen that the coating "copies" the substrate, attenuating its waviness. Adherence was optimal, and could only be eliminated with diamond paste.

The experience described was repeated with other substrates: copper, steel, glass and a sodium chloride crystal. It was verified that the characteristics obtained were substantially independent of the substrate used.

In the case of sodium chloride, after obtaining the coating, the substrate was dissolved in water, obtaining a self-sustaining film.

By rotating the substrate during the application of the procedure, the entire surface thereof can be coated.

SPECTROMETRIC CHARACTERISTICS OF THE FILMS OBTAINED

It is interesting to have an in-depth look into Raman spectroscopy.

The first order Raman spectrum of graphite (characterized by trigonal SP2 bonds) presents a sole acute peak at 1580 $cm^{-1}$. Diamond, characterized by tetrahedral SP3 bonds, also has a sole acute Raman active first order band at 1332 $cm^{-1}$.

When graphite becomes amorphous, its band goes down in frequency (up to 1500 $cm^{-1}$ approximately) and widens considerably, obtaining a spectrum more similar to state density calculated for an amorphous material made up to SP2 bonds.

The Raman spectrum of amorphous diamond is unknown. State density calculations, supposing SP3 bonds in an amorphous structure, also indicate a widened band between 1200 and 1300 $cm^{-1}$.

On the other hand, microcrystalline graphic presents, besides the 1580 $cm^{-1}$, a band of approximately 1350 $cm^{-1}$ (depending on the size of the granule).

Raman spectroscopy thus appears to be a sensitive tool, both for the crystalline and amorphous character of the sample, as well as for its composition in terms of SP2 and SP3 bonds.

In the samples obtained by application of the present procedure (including the self-sustaining film), a peak was obtained at 1295 $cm^{-1}$, which was corresponding to the structure of amorphous diamond.

To investigate this topic further, certain experiments were conducted, applying on appropriate (1,1,1) silicone substrates ion beams of C+ and $CH_3^+$ with various energies. Ions were selected with the magnetic separator.

With $C^+$ alone, and low energies (1 KeV) a sole peak was obtained, widened at 1545 $cm^{-1}$. When energy was increased to 10 KeV, a slight shoulder was formed, located at lower frequencies.

In exchange, with $CH_3^+$ alone, already at 1 KeV a peak was formed at 1520 $cm^{-1}$, as well as a shoulder (swelling in the scale corresponding to lower frequencies) which, when analyzed, corresponded to a second peak (of lower amplitude) at 1330 $cm^{-1}$.

At 10 KeV the shoulder was bigger, with the peak at 1500 $cm^{-1}$, and the second peak at 1300 $cm^{-1}$. Finally, at 30 keV, the first peak is at less than 1500 $cm^{-1}$, and the second peak at 1295 $cm^{-1}$.

In summary, in the case of the deposit with $C^+$ at low energies, a sole peak was obtained at 1545 $cm^{-1}$, which seems to indicate that SP2 bonds are predominant in the film formed and that, as the energy of the beam increases, a second peak appears. The same relation with energy is observed when bombarding with $CH_3^+$. The difference between the films obtained is that, in those formed with hydrogenated beams, there is always a second peak at lower frequencies, which seems to indicate that hydrogenated beams favor the formation of SP3 bonds.

The Raman spectra of the films obtained with plasma are similar to those obtained with hydrogenated beams. But, generally, the former present peaks concentrated at high frequencies.

It is noteworthy that the relative amplitude of the two peaks does not quantify the ratio between the number of SP2 and SP3 bonds, since spectroscopy does not give a lineal result. This quantifying task has not yet been performed.

The second peak was obtained by decomposing the Raman spectroscopy into the sum of the two Lorentz curves, by computer methods.

When the diamond-type films are heated to 700° C. in an inert atmosphere, they clearly present a peak at 1580 $cm^{-1}$, corresponding to graphite, and a second peak around 1360 $cm^{-1}$. This result is interpreted as the passing from a less stable stage (diamond) to another more stable stage (graphite) under the action of temperature. It is noteworthy that when a natural (crystalline) diamond is subjected to high temperatures, the same reaction takes place, with the difference that the temperatures at which this occurs are higher.

A study was made of the influence of an argon beam on the structure obtained by applying the present procedure; the Raman spectra before and after argon bombarding do not show changes in the structure of the deposit.

From the above explanation and the results obtained, it arises that it is possible to characterize the film formed by a net peak (not unique) at approximately 1295 $cm^{-1}$, presented in Raman spectroscopy, which does not appear in films obtained by other procedures.

It is presumed that the procedure described will enable obtaining films with similar characteristics and also with a significant proportion of SP3 bonds, i.e. which can be characterized by a peak similar to that described in the previous paragraph, forming the second beam with another carbo-hydrogenate, such as $CH_4^+$ instead of $CH_3^+$. It is anticipated that such variation, whose shortcoming is that these ions coincide in mass and charge with ions O+ which are difficult to eliminate, is included under the scope of the present invention.

The foregoing describes some examples of realization of the procedure for forming, on a solid substrate, an amorphous carbon film with properties similar to those of diamond, which is the main object of the present invention, whereby the scope of protection of the present invention is defined, mainly, by the appended claims.

It is further noted that other modifications may be made to the construction of the present invention, without departing from the spirit and scope of the appended claims.

We claim:

1. A process for forming on a solid substrate, a film of diamond-like carbon at ambient temperature, comprising the following steps:
   a) cleaning and degreasing the outer surfaces of said solid substrate;
   b) introducing said substrate, in a first chamber, which said chamber is substantially at ground potential, with a layout which also includes an ion source at a higher positive voltage as compared to the ground, the voltage variable between 1 and 70 KeV, and a path between said ion source and said first chamber in which are located, at least, one set of electrostatic lenses and one magnetic mass separator;
   c) creating a vacuum in said layout, on an order of $10^{-5}$ mbar;
   d) generating a first ion beam of $C^+$, or $CH_n^+$ where $n<5$ in said ion source, at a high positive voltage as compared to said ground;
   e) forming and concentrating said first ion beam with said set of electrostatic lenses;
   f) homogenizing said first beam with said magnetic mass separator, capable of deviating any undesired ions, and obtaining a second beam with carbon-hydrogenated ions consisting of $C^+$ and $C_n^+$, where $n<5$ ions; and
   g) subsequently applying only said second homogenized ion beam in said mass separator on the surface of said substrate, until said substrate is covered with said film of diamond-like carbon, wherein said ions of said second beam have an energy on the order of 30 keV, arising from the acceleration caused by the higher positive voltage as compared to ground the voltage variable being between 1 and 70 keV.

2. A process for forming on a solid substrate, a film of diamond-like carbon, as in claim 1, wherein said ion source used in stage d) is made up of a second chamber at a higher positive voltage as compared to said ground, the voltage variable between 1 and 70 keV, in which said second chamber there is a thermo-emitting hot filament, negative as compared to the walls of said second chamber, capable of providing electrons; said second chamber, equipped with a needle valve through which methane enters; thus establishing an arc between said filament and said walls, which said arc ionizes and fragments the methane molecules, producing $C^+$, $CH_3^+$ and $CH_4^+$ plasma.

3. A process for forming on a solid substrate, a film of diamond-like carbon, as in claim 1, wherein said second beam of carbon-hydrogenated ions is a beam of $CH_3^+$ ions.

4. A process for forming on a solid substrate, a film of diamond-like carbon, as in claim 1, wherein said substrate is permanently rotated in order to obtain total coating of said surface of said substrate.

5. A process for forming on a solid substrate, a film of diamond-like carbon, as in claim 1, wherein after stage g), said solid substrate is dissolved in a solvent, obtaining a self-sustaining diamond-like carbon film.

6. A process for forming, on a solid substrate, a film of diamond-like carbon, as in claim 1, wherein after stage g), the solid substrate is melted, obtaining a self-sustaining diamond-like carbon film.

7. A process for forming on a solid substrate, a film of diamond-like carbon, as in claim 1, wherein said second beam of carbon hydrogenated ions is a beam of $CH_4^+$ ions.

* * * * *

UNITED STATES PATENT AND TRADEMARK OFFICE
CERTIFICATE OF CORRECTION

PATENT NO. : 5,547,714
DATED : August 20, 1996
INVENTOR(S) : Hugo A. Huck et al

It is certified that error appears in the above—identified patent and that said Letters Patent is hereby corrected as shown below:

On the title page, Item
[75] Inventors:  Hugo A. Huck, Buenos Aires
Alberto E. Jech, Lujan
Raul Righini, Lujan
Emilia B. Halac, Buenos Aires
Maria A. R. de Benyacar, Martinez
Julio A. Nicolai, Moreno
All of Argentina Signed and Sealed this Twenty-second Day of April, 1997

Attest:

BRUCE LEHMAN

Attesting Officer

Commissioner of Patents and Trademarks